(12) United States Patent
Herzog et al.

(10) Patent No.: US 9,625,392 B2
(45) Date of Patent: Apr. 18, 2017

(54) DETECTING ORGANIC CONTAMINANTS

(71) Applicant: THONHAUSER GMBH, Giesshuebl (AT)

(72) Inventors: Daniel Herzog, Purkersdorf (AT); Philip Thonhauser, Giesshubl (AT)

(73) Assignee: THONHAUSER GMBH, Giessuebl (AT)

( * ) Notice: Subject to any disclaimer, the term of this patent is extended or adjusted under 35 U.S.C. 154(b) by 0 days.

(21) Appl. No.: 14/766,304

(22) PCT Filed: Feb. 7, 2014

(86) PCT No.: PCT/EP2014/052461
§ 371 (c)(1),
(2) Date: Nov. 18, 2015

(87) PCT Pub. No.: WO2014/122277
PCT Pub. Date: Aug. 14, 2014

(65) Prior Publication Data
US 2016/0061739 A1    Mar. 3, 2016

(30) Foreign Application Priority Data
Feb. 7, 2013   (EP) ..................................... 13154384

(51) Int. Cl.
*G01N 21/78*   (2006.01)
*G01N 33/52*   (2006.01)
(Continued)

(52) U.S. Cl.
CPC ............. *G01N 21/78* (2013.01); *A01N 59/02* (2013.01); *C11D 3/124* (2013.01); *C11D 3/1266* (2013.01);
(Continued)

(58) Field of Classification Search
CPC .... A01N 59/02; A01N 2300/00; A01N 59/00; C11D 11/0041; C11D 3/124;
(Continued)

(56) References Cited

U.S. PATENT DOCUMENTS

| | | | |
|---|---|---|---|
| 6,663,902 B1 * | 12/2003 | Hei ........................ | A01N 59/00 422/29 |
| 2007/0102665 A1 * | 5/2007 | Thonhauser ........... | A01N 59/02 252/186.1 |
| 2008/0142041 A1 * | 6/2008 | Fischer .................. | B01D 65/02 134/10 |

FOREIGN PATENT DOCUMENTS

| | | |
|---|---|---|
| DE | 102006060204 A1 | 6/2008 |
| GB | 1510452 A | 5/1978 |

(Continued)

OTHER PUBLICATIONS

International Search Report (with English translation) and Written Opinion issued May 12, 2014 in International Application No. PCT/EP2014/052461.

(Continued)

*Primary Examiner* — Jennifer Wecker
(74) *Attorney, Agent, or Firm* — Panitch Schwarze Belisario & Nadel LLP

(57) ABSTRACT

A composition including at least one strong oxidant, a color indicating system, and one or more thickening agents is provided. A method of using the composition on an aqueous basis includes detecting any contaminants on a surface with organic substances by visual control after superficially applying the composition to the surface. The composition is not flowable for a predefined period after the superficial application due to the effect of the thickening agent. The one or more thickening agents are stable in the composition during the predefined period, and are selected from synthetic sheet silicates, pyrogenic silicic acid, fatty alkyl (benzene)

(Continued)

sulfates, sulfonates, carboxylates, phosphates and aminoxides and mixtures thereof. A color change in the composition applied to the surface during the predefined period indicates that organic contaminants are present on a portion of the surface.

15 Claims, 1 Drawing Sheet

(51) Int. Cl.
G01N 31/22 (2006.01)
A01N 59/02 (2006.01)
C11D 3/39 (2006.01)
C11D 11/00 (2006.01)
C11D 3/12 (2006.01)
C11D 7/20 (2006.01)
A01N 59/00 (2006.01)
G01N 21/77 (2006.01)

(52) U.S. Cl.
CPC .............. *C11D 3/3947* (2013.01); *C11D 7/20* (2013.01); *C11D 11/0041* (2013.01); *G01N 31/22* (2013.01); *G01N 33/52* (2013.01); *G01N 2021/7796* (2013.01)

(58) Field of Classification Search
CPC ....... C11D 3/1266; C11D 3/3947; C11D 7/20; G01N 2021/7796; G01N 21/78; G01N 31/22
See application file for complete search history.

(56) References Cited

FOREIGN PATENT DOCUMENTS

| WO | 9932596 A1 | 7/1999 | |
| WO | WO 9932596 A1 * | 7/1999 | ............. C11D 3/042 |
| WO | 0223993 A2 | 3/2002 | |
| WO | 0231098 A1 | 4/2002 | |
| WO | 2005044968 A1 | 5/2005 | |

OTHER PUBLICATIONS

Search Report issued in EP Application No. 13154384.

* cited by examiner

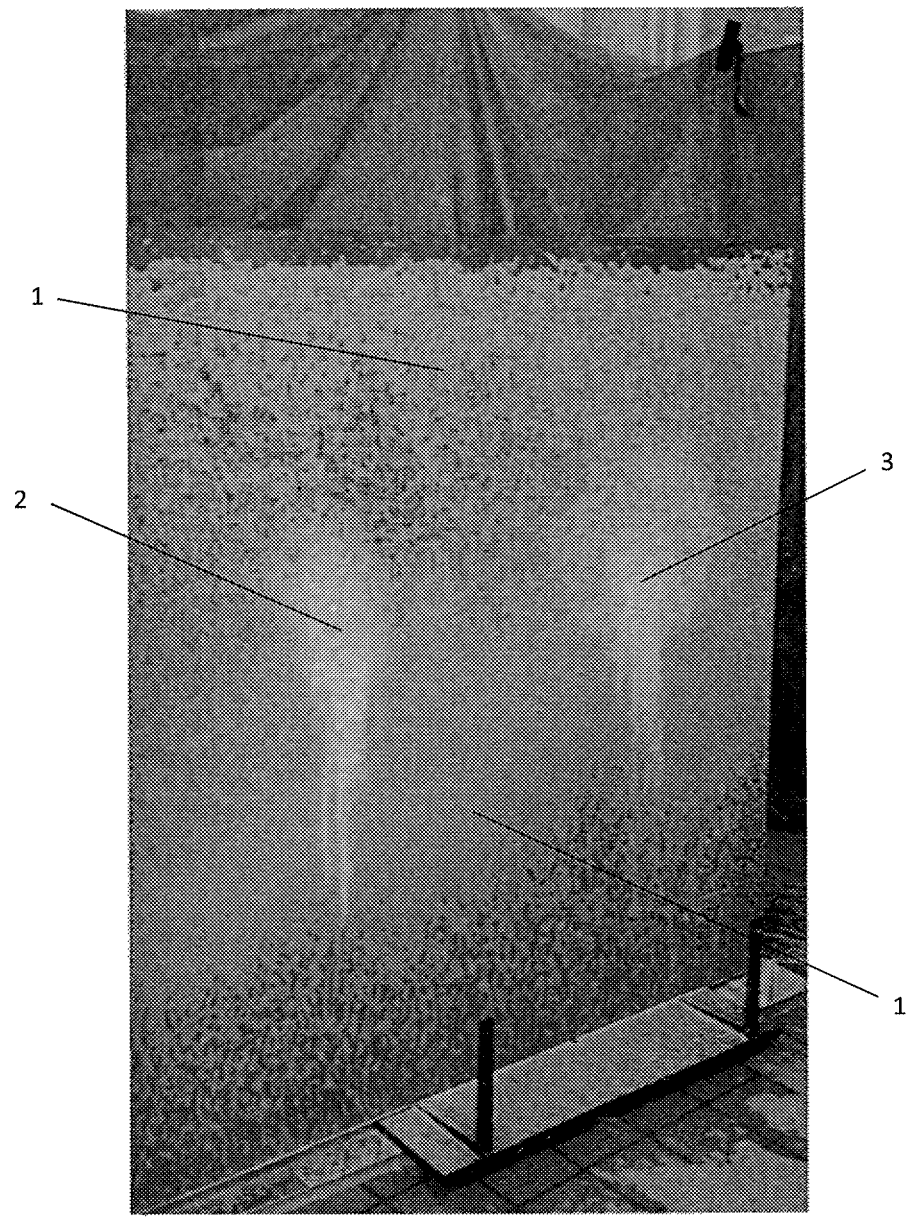

DETECTING ORGANIC CONTAMINANTS

CROSS-REFERENCE TO RELATED APPLICATIONS

This application is a Section 371 of International Application No. PCT/EP2014/052461, filed Feb. 7, 2014, which was published in the German language on Aug. 14, 2014, under International Publication No. WO 2014/122277 A1 and the disclosure of which is incorporated herein by reference.

BACKGROUND OF THE INVENTION

The present invention relates to the use of a highly oxidizing composition for detecting any contaminants on a surface with organic substances.

Detergents and disinfectants that contain strong oxidants have been known for a long time Such compositions are described in various prior art patents. European Patent No. EP 1,343,864 B1 discloses a detergent and disinfectant containing a water-soluble permanganate, which additionally includes a pH adjusting agent for securing an alkaline milieu of at least pH 10, preferably at least pH 12, such as NaOH, for example, as well as at least one other oxidant having an oxidative potential higher than that of manganese (VII) to manganese(VI), and preferably above that of $HO_2^-$ to $OH^-$, preferably a pemxydisulfate.

Such a composition will unfold its oxidative effect in a highly alkaline milieu predominantly by reducing Mn(VII) to Mn(VI), whereby the latter will be simultaneously oxidized to oxalate if organic carbon is present. The other oxidant having an oxidative potential higher than that of manganese(VII), such as one or more alkali metal peroxydisulfates, for example, will react more slowly with organic carbon as a permanganate, such that, upon dissolution of the powdery composition in water, there will first be oxidation of hydroxide ions to hydrogen peroxide ions due to both the peroxydisulfate and the permanganate, which is reduced to Mn(VI) in the process. See the following Equations 1 and 2:

$$3OH^- + S_2O_8^{2-} \to HO_2^- + 2SO_4^{2-} + H_2O \qquad \text{Equation 1}$$

$$4OH^- + 4MnO_4^- \to O_2\uparrow + 4MnO_4^{2-} + 2H_2O \qquad \text{Equation 2}$$

The resulting hydrogen peroxide ion may, however, cause re-oxidation of Mn(VI) to Mn(VII).

$$HO_2^- + 2MnO_4^{2-} + H_2O \to 3OH^- + 2MnO_4^- \qquad \text{Equation 3}$$

When the disintegration rate of the peroxydisulfate cannot catch up with that of the permanganate (e.g. because disintegration of the permanganate is favored by high concentration and/or good oxidability), increased formation of Mn(VI) will occur. The predominance of the hexavalent manganese species results in a green color of the solution as opposed to the initial purple coloration due to Mn(VII). The oxidation of organic compounds (here referred to as "CH₂O" in representation of the oxidation step ±0 and in particular of carbohydrates) to oxalate by Mn(VII) and the associated reduction of the permanganate is quick in any case, as the high pH has an anionizing effect on numerous organic materials, facilitating targeting of anionic oxidants. The oxidation of organic substances by Mn(VII) also involves $MnO_4^{3-}$, in which manganese having the atomic number +5 is present (Equation 4) but may be re-oxidized to hexavalent manganese by permanganate (Equation 5):

$$2\{CH_2O\} + 3MnO_4^- + 2H_2O \to C_2O_4^{2-} + 3MnO_4^{3-} + 8H^+ \qquad \text{Equation 4}$$

$$MnO_4^{3-} + MnO_4^- \to 2MnO_4^{2-} \qquad \text{Equation 5}$$

Targeting organic substances with permanganate according to Equation 4, however, does not require the high efficacy of such a combination of permanganate and peroxydisulfate. Instead, quick and efficient oxidation of organic materials is caused by now starting radical reactions. Their starting point are $SO_4^-$ radicals that may result from the peroxydisulfate by hemolytic cleavage of peroxydisulfate (Equation 6) or by reacting the same with organic compounds (Equation 7) (herein, compounds in bold indicate radicals or radical ions):

$$S_2O_8^{2-} \to 2SO_4^- \qquad \text{Equation 6}$$

$$2S_2O_8^{2-} + 2\{CH_2O\} + 2H_2O \to 2SO_4^{2-} + 2SO_4^- + \{C^{+1}-R\} + 4H^+ \qquad \text{Equation 7}$$

in which $\{C^{+1}-R\}$ represents a radical with carbon in oxidation step +1, such as formally $\{H_2C_2O_3\}^{2-}$, in which there is a double bond between the carbon atoms.

Primarily, however, sulfate radicals seem to be generated by reacting Mn(V) (see equation 4 above) with peroxydisulfate (Equation 8):

$$MnO_4^{3-} + S_2O_8^{2-} \to MnO_4^{2-} + SO_4^{2-} + SO_4^- \qquad \text{Equation 8}$$

In the process, Mn(V) is re-oxidized to Mn(VI). Eventually, based on the thermodynamic instability of Mn(VI), predominantly Mn(II) is formed:

$$MnO_4^{2-} + H_2O \to O_2\uparrow + HMnO_2^- + OH^- \qquad \text{Equation 9}$$

The Mn(II) causes the composition to have a yellow color. Such a color can also be interpreted as an indication that the oxidants were consumed by large amounts of contaminants. Mn(II) is slowly oxidized to Mn(IV) by atmospheric oxygen, and the Mn(IV) can eventually sediment in the form of manganese dioxide ($MnO_2$).

Combinations of permanganate and peroxydisulfate therefore display a synergistic effect in oxidizing organic carbon and at the same time provide an indication system, as the initially purple solution assumes an easily visible green color in the presence of organic carbon. As possible alternatives to peroxydisulfate, periodate, peroxydiphosphate, ozone and hypochlorite are mentioned.

According to European Patent No. EP 1,343,864 B1, the detergent and disinfectant can be used for cleaning drinks dispensing apparatuses (by flushing the apparatus with the aqueous solutions) or contaminated bottles from organic residues or for cleaning surfaces in vegetable processing plants or breweries, albeit in the latter case for removing inorganic plaque—after the agent has acted on the plaque "for less than one hour".

An improvement of the detergent and disinfectant is disclosed in European Patent No. EP 1,730,258 B1, in which pH buffering substances, preferably alkali metal (hydrogen) carbonates as well as anti-oxidant polyphosphates are added.

In European Patent No. EP 1,456,338 B1, combinations of water-soluble chlorite and bromate, which are also stabilized using a pH regulator at a highly alkaline pH to suppress the formation of chlorine dioxide, are disclosed. As applications, again drinks dispensing apparatuses, as well as pipelines in the dairy and beverage industries, as well as the processing of swimming pool water are mentioned.

A drawback of these prior-art detergents is that the aqueous solutions are mostly only 1-3% solutions of the contained oxidant. While these solutions are perfectly well usable in containers or conduits, they quickly drain off surfaces when the surface is not an exact horizontal plane, best with an elevated boundary. Particularly in the case of smooth stainless steel surfaces or ceramic tiles, as they are commonly used in the beverage or food industries, reliably cleaning surfaces is impossible, especially when they are tilted or vertical surfaces. Another drawback is manganese dioxide formation, as manganese dioxide is not soluble in water and therefore hardly removable using the means described above.

It is an aim of the present invention to overcome these drawbacks. Another aim of the invention is to develop a method enabling visual control of the degree of contamination of industrial surfaces.

BRIEF SUMMARY OF THE INVENTION

The present invention achieves the above aims by providing a new method for using an aqueous-based composition comprising:
a) at least one strong oxidant,
b) a color indication system, and
c) one or more thickening agents
for detecting any contaminants on a surface with organic substances by visual control after superficially applying the composition to the surface, the composition not being flowable for a predefined period after superficial application due to the effect of the thickening agent,
the thickening agent(s) being stable in the composition during the predefined period; and
the thickening agent(s) being selected from synthetic sheet silicates, pyrogenic silicic acid, fatty alkyl (benzene) sulfates, sulfonates, carboxylates, phosphates and aminoxides and mixtures thereof;
and a color change in the composition applied to the surface during the predefined period indicating organic contaminants on said site of the surface.

The present invention is based on a plurality of surprising discoveries made by the inventors: Firstly, that the addition of a thickening agent to an aqueous composition comprising at least one oxidant and a color indication system not only thickens the composition according to its purpose, and thereby limits its flowability, but also has a stabilizing effect on the oxidant and thus on the color development. Secondly, that not only inorganic but also organic thickeners, such as organic surfactants, for example, can be used as thickening agents, although the strong oxidant is supposed to oxidize organic contaminants very quickly as will be explained in detail below.

Without wishing to be bound by theory, it is assumed that the stabilizing effect on the oxidant is based on the limited mobility of the ions in the thickened solution and the simultaneously limited entry of atmospheric oxygen. When permanganate is used as an oxidant, as preferred according to the present invention, this suppresses both the formation on Mn(II) species, and thus the yellowing of the composition and the resulting oxidation of Mn(II) to Mn(IV). The thickener thus stabilizes the color of the composition—purple in the absence of organic contaminants, green in the presence thereof—and at the same time reduces the formation of manganese dioxide sediments that are difficult to remove using aqueous solutions.

The type and amount of thickening agent are preferably selected such that the composition is given, at least for a predefined period, a consistency that causes it essentially not to drain or drop off tilted, curved or vertical surfaces such as pipes or walls, or even downward facing surfaces such as ceiling tiles or the like.

"Essentially not flowable" herein means a consistency of the composition in which it is thickened to such an extent that a layer of the composition applied superficially to a vertical surface does not flow downwards by more than 10 cm, preferably more than 5 cm, in particular more than 2 cm, during the predefined period. It is therefore possible according to, the present invention to determine very accurately not only the presence but the position of contaminants on the surface to be tested.

While the predefined period is partly dependent on the concentration of the oxidant(s) as well as on the type of thickening agent—inorganic, organic or both—, it is preferably at least 10 seconds, more preferably at least 20 seconds, even more preferably at least 15 seconds, and even more preferably at least 1 minute, in order to be able to oxidize all contaminants that might be present on the surface during this period.

The at least one oxidant is preferably selected from permanganates, peroxydisulfates, salts of halogen oxoacids and mixtures thereof all of which are strong oxidants capable of very quickly oxidizing organic contaminants. In particularly preferred embodiments, the oxidant comprises permanganate, as its use at the same time provides a color indication system. When using other oxidants as the permanganate, a person of skill in the art has a variety of usable indication systems at their disposal, including potassium iodide, dichromate or dichlorophenolic indophenole in combination with hydrogen peroxide or ferroin for persulfate.

Preferably, the composition comprises, next to permanganate, at least one additional oxidant whose oxidation potential exceeds that of permanganate to be able to use the initially described re-oxidation and synergy effects. Particularly preferably, the additional oxidant is selected from peroxydisulfate, hypochlorite and mixtures thereof and is used as the main oxidant in particularly preferred embodiments of the invention, i.e. it is contained in the composition at a higher amount than the permanganate, which is preferably at least 10 times, more preferably at least 20 times, even more preferably at least 30 times, the amount of permanganate, and preferably at least 0.3 g/L, as will be clear from the examples below.

As described above, the thickening agent(s) is/are selected from synthetic sheet silicates, pyrogenic silicic acid, fatty alkyl (benzene) sulfates, sulfonates, carboxylates, phosphates and aminoxides and mixtures thereof, as the inventors surprisingly found during their research that: a) natural inorganic thickeners, such as bentonite, for example, that obviously contain non-negligible amounts of organic contaminants, or organically modified natural thickeners, such as various Optigel® thickeners, are not stable during use according to the invention but targeted by the at least one oxidant; although b) certain organic thickeners, namely fatty alkyl (benzene) sulfates, sulfonates, carboxylates, phosphates, and aminoxides, unlike most other organic thickening agents do indeed have sufficient stability for the inventive use, as long-chained alkyl and phenyl groups seem to be sufficiently oxidation-resistant, at least for the predefined period.

Such organic thickening agents are preferably contained at a total amount of not more than 3% by weight, more preferably not more than 2% by weight, in particular not more than 1% by weight, of the entire composition to guarantee stability even prior to use.

For example, combinations of inorganic and organic thickening agents, e.g. made of a sheet silicate and an organic surfactant, have the additional advantage next to the mutually exerted thickening effect that the inorganic thickener is primarily responsible for the stabilizing effect on the manganese species, while the organic surfactant provides for any manganese dioxide that might have formed nevertheless to be removable from the inspected surface more easily.

Preferably, the composition further comprises one or more adjuvants that are particularly preferably selected from pH regulators, hardness stabilizers and biocides. For example, the use of some oxidants or combinations thereof requires adjusting the pH of the composition to highly alkaline levels, such as at least 10 or 11, for which purpose NaOH or KOH are used particularly preferably. While other strong bases can also be used, these are not preferred for cost concerns.

In preferred embodiments of the invention, the surface is simultaneously cleaned by superficially applying the composition, i.e. after visual control whether and where the surface is contaminated, the composition—optionally after an additional time of exposure exceeding the predefined period—can be removed together with all organic or inorganic residues, which is preferably done by simply rinsing the surface with cold water, optionally followed by wiping the surface, e.g. with wet tissues or squeegees.

Visual control can be with the naked eye when the color indicator used reveals a sufficiently distinct color change, but it can also be computer-assisted by conducting digital color comparisons. The latter is preferable when the degree of contamination of the surface to be tested is very low and therefore the color change of the indicator is minor. For this purpose, a digital camera can be used to take a photograph of the surface to be tested after superficially applying the composition and allowing sufficient exposure time to pass and the photograph can be compared with a preset color scale using a color comparison software, e.g. by converting the colors on the photograph, or at least a section thereof, to RGB grades.

BRIEF DESCRIPTION OF THE DRAWINGS

The foregoing summary, as well as the following detailed description of the invention, will be better understood when read in conjunction with the appended drawing. For the purpose of illustrating the invention, there is shown in the drawing, an embodiment which is presently preferred. It should be understood, however, that the invention is not limited to the precise arrangements and instrumentalities shown.

In the drawing:

The FIGURE is a photograph showing the results of a detection test of Example 40, according to an embodiment of the present invention, on a deliberately contaminated, vertical stainless-steel surface.

DETAILED DESCRIPTION OF THE INVENTION

In the following, the present invention will now be described in more detail based on specific, non-limiting exemplary embodiments and comparative examples.

EXAMPLES

Compositions for use in a method according to the present invention were prepared by dissolving potassium permanganate and a second strong oxidant selected from sodium hypochlorite (HC) and sodium peroxydisulfate (PS) together with one commercially available, inorganic or organic thickening agent (TA) each in the following proportions in water by stirring:

| | |
|---|---|
| $KMnO_4$ | 0.01 g |
| HC or PS | 0.12 g |
| NaOH | 0.04 g |
| TA | 0.5 to 7 g |
| water | to 100 ml |

Examples 1 Through 38 and Comparative Examples 1 Through 82—Stability Tests

Solutions prepared as described above were measured in a photoreader while examining whether the ratio between Mn(VII) and Mn(VI) was above 75% over a period of 20 min. Afterwards, 0.5 ml of a 0.1% glucose solution were added, and the color gradient was observed over a period of 10 min. A composition was regarded as stable when the Mn(VII)/Mn(VI) ratio was above 75% and a clear color change from purple to green occurred.

The exact amounts of the respective thickening agents are given in Tables 1 and 2 below, together with the evaluation "+" for stable or "−" for not stable, where organic thickening agents were tested in Examples 1 through 34 and Comparative Examples 1 through 72 (i.e., CE 1-72) (Table 1) and inorganic thickening agents were tested in Examples 35 through 38 and Comparative Examples 73 through 82 (i.e., CE 73-82) (Table 2). In the tables, the commercial names, the manufacturer and, if known, the active substance or at least its substance class are given in the tables. However, the other adjuvant materials of the commercial products were completely unknown in a vast majority of cases, because such manufacturer information was mostly missing.

This is also why no generally applicable statements can be made with regard to the suitability of commercially available products in the present invention. Nevertheless, a detailed interpretation of the achieved results can be found below the tables.

Most commercial names of thickening agents are branded. Nevertheless, marking every single one of them with® or™ in the tables was omitted for convenience purposes.

TABLE 1

| Organic Thickening Agents | | | | | | |
|---|---|---|---|---|---|---|
| Example # | Thickening Agent | Manufacturer | Active Substance | Ox. 2 | Thickener (wt. %) | Rating |
| Example 1 | Dowfax 2A1 | Dow | branched C12 alkyl cliphenyloxide disulfonate | PS | 2 | + |
| CE 1 | -"- | -"- | -"- | -"- | 7 | − |
| Example 2 | -"- | -"- | -"- | HC | 2 | + |
| CE 2 | -"- | -"- | -"- | -"- | 7 | − |
| Example 3 | Dowfax 3B2 | -"- | linear C10 alkyl diphenyl sulfonate | PS | 2 | + |
| Example 4 | -"- | -"- | -"- | -"- | 7 | + |
| Example 5 | -"- | -"- | -"- | HC | 2 | + |

TABLE 1-continued

Organic Thickening Agents

| Example # | Thickening Agent | Manufacturer | Active Substance | Ox. 2 | Thickener (wt. %) | Rating |
|---|---|---|---|---|---|---|
| Example 6 | -"- | -"- | -"- | -"- | 7 | + |
| CE 3 | Methocel 267 | -"- | cellulose ether | PS | 1 | − |
| CE 4 | -"- | -"- | -"- | HC | 1 | − |
| CE 5 | Rhodopol 23 | Rhodia | xanthane gum | PS | 1 | − |
| CE 6 | -"- | -"- | -"- | HC | 1 | − |
| Example 7 | Genarninox LA | Clariant | lauryl dimethyl aminoxide | HC | 2 | + |
| CE 7 | -"- | -"- | -"- | -"- | 7 | − |
| Example 8 | Genaminox CSL | -"- | coconut alkyl dimethyl aminoxide | PS | 2 | + |
| CE 8 | -"- | -"- | -"- | -"- | 7 | − |
| CE 9 | -"- | -"- | -"- | HC | 2 | − |
| CE 10 | -"- | -"- | -"- | -"- | 7 | − |
| CE 11 | Genamin CC 302D | -"- | coconut alkyl dimethyl amine | HC | 0.5 | − |
| CE 12 | -"- | -"- | -"- | -"- | 3 | − |
| CE 13 | Sandoperm CAN | -"- | amino-modified silicone elastomer | -"- | 0.5 | − |
| CE 14 | -"- | -"- | -"- | -"- | 3 | − |
| Example 9 | Akyposoft 100 BCEC | KAO | polyoxyethylene-(11) lauryl ether carboxylate-Na | PS | 2 | + |
| Example 10 | -"- | -"- | -"- | -"- | 7 | + |
| CE 15 | -"- | -"- | -"- | HC | 2 | − |
| CE 16 | -"- | -"- | -"- | -"- | 7 | − |
| Example 11 | Oxidet DM-20 | -"- | dimethyl lauraminoxide | PS | 2 | + |
| Example 12 | -"- | -"- | -"- | -"- | 7 | + |
| Example 13 | -"- | -"- | -"- | HC | 2 | + |
| Example 14 | -"- | -"- | -"- | -"- | 7 | + |
| Example 15 | Oxidet L-75 C | -"- | coconut alkyl amidopropylaminoxide | PS | 2 | + |
| CE 17 | -"- | -"- | -"- | -"- | 7 | − |
| CE 18 | -"- | -"- | -"- | HC | 2 | − |
| CE 19 | -"- | -"- | -"- | -"- | 7 | − |
| CE 20 | Amidet A-15 | -"- | polyoxyethylene-(2) tridecyl ether carboxylic acid ethanolamide | HC | 0.5 | − |
| CE 21 | -"- | -"- | -"- | -"- | 3 | − |
| CE 22 | Betadet HR-50K | -"- | coconut alkyl amido propyl betaine | HC | 2 | − |
| CE 23 | -"- | -"- | -"- | -"- | 7 | − |
| CE 24 | Betadet S-20 | -"- | lauryl hydroxysulfobetaine | PS | 2 | − |
| CE 25 | -"- | -"- | -"- | -"- | 7 | − |
| CE 26 | -"- | -"- | -"- | HC | 2 | − |
| CE 27 | -"- | -"- | -"- | -"- | 7 | − |
| CE 28 | Betadet SHR | -"- | coconut alkyl amidopropyl hydroxysulfobetaine | PS | 2 | − |
| CE 29 | -"- | -"- | -"- | -"- | 7 | − |
| CE 30 | -"- | -"- | -"- | HC | 2 | − |
| CE 31 | -"- | -"- | -"- | -"- | 7 | − |
| Example 16 | Quartamin AB | -"- | behenyl trimethyl ammonium chloride | HC | 2 | + |
| Example 17 | -"- | -"- | -"- | -"- | 7 | + |
| Example 18 | Emal 30E | -"- | sodium lauryl sulfate | PS | 0.5 | + |
| Example 19 | -"- | -"- | -"- | -"- | 2 | + |
| CE 32 | -"- | -"- | -"- | -"- | 3 | − |
| CE 33 | -"- | -"- | -"- | -"- | 7 | − |
| CE 34 | -"- | -"- | -"- | HC | 2 | − |
| CE 35 | -"- | -"- | -"- | -"- | 7 | − |
| CE 36 | Emal 10N | -"- | sodium lauryl sulfate | HC | 0.5 | − |
| CE 37 | -"- | -"- | -"- | -"- | 3 | − |
| CE 38 | SerCEo AM 1010 | Elementis | coconut alkyl aminopropionate | HC | 0.5 | − |
| CE 39 | -"- | -"- | -"- | -"- | 3 | − |
| CE 40 | Serdox NBS 6.6/90 | -"- | polyoxyethylene-(6,6)-$C_{9-11}$-alkylether | PS | 2 | − |
| CE 41 | -"- | -"- | -"- | -"- | 7 | − |
| CE 42 | -"- | -"- | -"- | HC | 2 | − |
| CE 43 | -"- | -"- | -"- | -"- | 7 | − |
| CE 44 | Serdox NBSQ 5/5 | -"- | polyoxyethylene-(5)-polyoxypropylene-(5)-$C_{9-11}$-alkylether | PS | 2 | − |
| CE 45 | -"- | -"- | -"- | -"- | 7 | − |
| CE 46 | Sermul EA 266 | -"- | polyoxyethylene-(15)-tridecylethersulfate-Na | PS | 2 | − |
| CE 47 | -"- | -"- | -"- | -"- | 7 | − |
| CE 48 | -"- | -"- | -"- | HC | 2 | − |
| CE 49 | -"- | -"- | -"- | -"- | 7 | − |
| CE 50 | SerCEo X13 90 | -"- | mixture of (quat. ammonium-) kationic and anionic surfactants | PS | 2 | − |
| CE 51 | -"- | -"- | -"- | -"- | 7 | − |
| CE 52 | SerCEo XB 90 | - | mixture of (quat. ammonium-) kationic and anionic surfactants | HC | 2 | − |
| CE 53 | -"- | -"- | -"- | -"- | 7 | − |
| CE 54 | SerCEo Q 8010 | -"- | Lauryl amidopropyl trimethylammonium methylsulfate | PS | 2 | − |
| CE 55 | -"- | -"- | -"- | -"- | 7 | − |
| CE 56 | -"- | -"- | -"- | HC | 2 | − |
| CE 57 | -"- | -"- | -"- | -"- | 7 | − |

TABLE 1-continued

Organic Thickening Agents

| Example # | Thickening Agent | Manufacturer | Active Substance | Ox. 2 | Thickener (wt. %) | Rating |
|---|---|---|---|---|---|---|
| Example 20 | Crodasinic LS30 NP | Croda | sodium fatty acyl sarcosinate | PS | 2 | + |
| CE 58 | -"- | -"- | -"- | -"- | 7 | − |
| Example 21 | -"- | -"- | -"- | HC | 2 | + |
| CE 59 | -"- | -"- | -"- | -"- | 7 | − |
| Example 22 | Multitrope 1214 | -"- | fatty alkyl phosphate ester | HC | 0.5 | + |
| Example 23 | -"- | -"- | -"- | -"- | 3 | + |
| Example 24 | Poro TS 430X | Poro | | PS | 2 | + |
| Example 25 | -"- | -"- | -"- | -"- | 7 | + |
| CE 60 | -"- | -"- | -"- | HC | 2 | − |
| CE 61 | -"- | -"- | -"- | -"- | 7 | − |
| Example 26 | Hoesch L29 | J. Hoesch | polyoxyethylene-(3)-laurylethersulfosuccinate-2Na | HC | 0.5 | + |
| CE62 | -"- | -"- | -"- | -"- | 3 | − |
| Example 27 | Plurafac LF 221 | BASF | polyalkylenoxide fatty alkylether | PS | 2 | + |
| CE 63 | -"- | -"- | -"- | -"- | 7 | − |
| CE 64 | -"- | -"- | -"- | HC | 2 | − |
| CE 65 | -"- | -"- | -"- | -"- | 7 | − |
| CE 66 | Lutensol GD 70 | -"- | fatty alkylpolyglucosicle | HC | 2 | − |
| CE 67 | -"- | -"- | -"- | -"- | 7 | − |
| Example 28 | Lutensol TO 89 | -"- | polyoxyethylene-$C_{13}$-isoalkylether | PS | 2 | + |
| Example 29 | -"- | -"- | -"- | -"- | 7 | + |
| CE 68 | -"- | -"- | -"- | HC | 2 | − |
| CE 69 | -"- | -"- | -"- | -"- | 7 | − |
| Example 30 | Glanapon DA 363 | Bussetti | modified silicone | PS | 0.5 | + |
| CE 70 | -"- | -"- | -"- | -"- | 3 | − |
| CE 71 | Acticide PHB 20 | Thor | polyhexamethylene biguanide | HC | 0.5 | − |
| CE 72 | -"- | -"- | -"- | -"- | 3 | − |
| Example 31 | Ammonyx LO | Stepan | dodecane aminoxide | PS | 0.5 | + |
| Example 32 | -"- | -"- | -"- | -"- | 3 | + |
| Example 33 | -"- | -"- | -"- | HC | 0.5 | + |
| Example 34 | -"- | -"- | -"- | -"- | 3 | + |

TABLE 2

Inorganic Thickening Agents

| Example # | Thickening Agent | Manufacturer | Active Substance | Ox. 2 | Thickener (wt. %) | Rating |
|---|---|---|---|---|---|---|
| CE 73 | Laponite EP | Rockwood | organically modified natural sheet silicate | PS | 1 | − |
| CE 74 | -"- | -"- | -"- | HC | 1 | − |
| Example 35 | Laponite RD | -"- | synthetic sheet silicate | PS | 1 | + |
| Example 36 | -"- | -"- | -"- | HC | 1 | + |
| CE 75 | Optigel CK | -"- | natural bentonite | PS | 1 | − |
| CE 76 | -"- | -"- | -"- | HC | 1 | − |
| CE 77 | Optigel WX | -"- | organically modified natural sheet silicate | PS | 1 | − |
| CE 78 | -"- | -"- | -"- | HC | 1 | − |
| CE 79 | Optigel W724 | -"- | organically modified smectite | PS | 1 | − |
| CE 80 | -"- | -"- | -"- | HC | 1 | − |
| CE 81 | Optigel WA | -"- | activated smectite | PS | 1 | − |
| CE 82 | -"- | -"- | -"- | HC | 1 | − |
| Example 37 | HDK D1515B | Wacker | pyrogenic silicic acid | PS | 1 | + |
| Example 38 | -"- | -"- | -"- | HC | 1 | + |

Without wishing to be bound by theory and with the limitation mentioned above that the adjuvant materials of the active substance formulated into the above commercial products were unknown, the following can be derived from the above Table 1:

Peroxydisulfate (PS) is preferable to hypochlorite (HC) as the second strong oxidant when organic surfactants are to be used as thickening agents. Further, the amount of organic surfactants to be used is to be minimized to guarantee the stability of the composition for a sufficient amount of time. Although some surfactants remain stable in a proportion of 7% by weight, others will cause a reaction even at above 2% by weight. The concentration of the organic surfactant in the composition should therefore preferably not exceed 3% by weight, more preferably not exceed 2% by weight. If this amount is not sufficient for the desired limitation of flowability, one or more inorganic thickening agents can additionally be added, which also entails advantages for removing inorganic residues, as mentioned above.

Regarding the material classes of the organic surfactants, anionic surfactants such as fatty alkyl (benzene) sulfates, sulfonates, carboxylates, and phosphates, tend to be more stable than cationic surfactants such as fatty alkyl ammonium salts or (in highly alkaline milieus) neutral molecules such as fatty alkyl amines, amphoteric surfactants (betaines) or non-ionogenic surfactants. While the latter, such as polyalkylene oxide fatty alkyl ether, were occasionally stable, it would be better to modify them with anionic groups. An exception are fatty alkyl aminoxides that provided very goos results. Polysaccharides such as cellulose and xanthane derivatives were not stable as expected, which should be due to the easy oxidability of the numerous OH groups. Among the two silicone derivatives tested, one was suitable at a low amount, but its exact modification was not known. The other one, an amino-modified silicone elastomer, was not even stable at an amount of 0.5% by weight.

Table 2 including the results achieved with inorganic thickening agents shows that both synthetic phyllosilicate and pyrogenic silicic acid (also referred to as amorphous silicic acid) are suitable for use as thickening agents in the composition. Again, it depends on the modification whether a sufficiently stable composition can be maintained or not. Without wishing to be bound by theory, it is assumed that natural products contain too large amounts of organic contaminants that are targeted by the oxidants, resulting in false detection results. The same is true to an even greater extent for organically modified, inorganic thickening agents.

A person of average skill in the art is able to determine a suitable synthetic, inorganic thickening agent and/or an organic thickening agent as falling within the selection according to the present invention for an otherwise predetermined composition conveniently and without undue experimentation, but by means of simple serial experiments based on their general knowledge in the art and using the instructions herein.

Examples 39 to 42 and Comparative Example 83—Vertical Surface

Compositions of the thickening agents, Dowfax 2A1 (analogous to Example 1 but using 0.5% by weight of thickening agent), Ammonyx LO (analogous to Example 33), Laponite RD (analogous to Example 35, but using 1.5% by weight of thickening agent), and HDK D1515B (analogous to Example 37, but using 1.5% by weight of thickening agent), i.e. two organic (fatty alkyl diphenyl oxide disulfonate; dodecane aminoxide) and two inorganic thickening agents (sheet silicate; pyrogenic silicic acid), were prepared as compositions of Examples 39 to 42. A corresponding composition without using thickening agent but peroxydisulfate as a second oxidant served as Comparative Example (CE) 83.

All four compositions were sprayed onto a vertical stainless steel surface to which one stroke of a 0.1%, or 0.01%, glucose solution, was previously applied and dried to obtain a glucose amount of about 1 mg/100 $cm^2$, or 0.1 g/100 $cm^2$, respectively, as the organic "contaminant" of the surface.

The compositions of Example 39 (Dowfax 2A1) and Example 50 (Ammonyx LO) were each present as a stable foam, that of Example 41 (Laponite RD) as a thixotropic gel and that of Example 42 (HDK D1515B) as a thixotropic liquid.

The compositions of Example 39 through 42 that first had a purple color changed their color to green at the contaminated spots on the surface within 30-120 seconds, indicating the presence of the organic contaminant. The green color was then maintained for 1-2 minutes each without observing a visible shift of the composition by flowing off.

In the composition of Comparative Example (CE) 83 that did not have thickening agent hardly any visible discoloration was observed as it immediately ran off the surface. Also, based on the therefore low sheet thickness, no color recognition was possible.

Contrary to that, the composition of Examples 39 through 42 turned out to be highly sensitive. The FIGURE shows a black and white photograph of the test of Example 40 about 10 minutes after application of the composition onto the surface (when the foam had already begun running off the surface). Reference numeral 1 indicates the non-discolored, darker portion of the foam (which was in fact stained purple), while reference numeral 2 indicates the lighter portion (actually stained green) in the left half that was more heavily contaminated (1 mg glucose/100 $cm^2$) and reference numeral 3 indicates the lighter portion (stained green) in the less contaminated right half (0.1 mg glucose/100 $cm^2$).

It can be discerned that the discoloration on the right is slightly less intense but still very clearly visible to the naked eye. The contamination is clearly detectable in both cases.

The present invention is thus able to quickly and reliably detect even organic contaminants at an amount of only 0.1 mg/100 $cm^2$ so that they are clearly discernible, even though an organic surfactant was also used as a thickening agent in Example 40 shown in the FIGURE. The latter obviously did not display a false-positive result over 10 min (because otherwise the entire foam would have had to change color).

Smaller amounts of contaminants can, of course, also be detected, either still with the naked eye or by conducting a computer-assisted digital color comparison. Such comparison can, for example, be made by taking a photograph of the surface covered with the composition using a digital camera and comparing the photograph with a given color scale using color comparison software, e.g. by converting the colors on the photo, or at least a relevant section thereof, to RGB values.

As a result, residual contaminants can be even detected on surfaces already subjected to cleaning using the present invention. The present invention is therefore perfectly suitable for the quality control of cleaning processes in industrial plants.

Example 43—Surface Facing Downwards

A gelatinous, thixotropic composition formed with the sheet silicate Laponite RD at an amount of 1.5% by weight as a thickening agent (analogous to Example 41) was sprayed onto the bottom side of a stainless steel plate that had been prepared with glucose as an organic contaminant in a manner analogous to Examples 39 through 42 above. Again, green coloration appeared within 30 seconds and remained visible during the following 5 minutes. The composition did not exhibit any tendency to drip off during this period.

Examples 44 Through 58 and Comparative Examples 84 and 85—Manganese Dioxide Formation Compositions were prepared as indicated above—each with peroxydisulfate as the second oxidant—using the types and amounts of thickening agents listed in Table 3 below and examined for manganese dioxide formation.

For this purpose, 100 ml of each composition—optionally together with 1 ml of a 0.01% glucose solution as the "contaminant"—were filled into a transparent glass bottle, a small stainless steel metal plate was immersed into the liquid, the bottle was sealed and allowed to stand for 20 minutes. Subsequently, the metal plate was removed and visually inspected for adherent manganese dioxide residues, as was the bottle wall. The observed amounts of adhering manganese dioxide were evaluated as follows:
− no manganese dioxide sediments visible
+ minimum amounts of manganese dioxide sediments
++ visible amounts of manganese dioxide sediments
+++ high amounts of manganese dioxide sediments
++++ very high amounts manganese dioxide sediments.

It is clearly discernible from Table 3 on the following page that the amount of manganese dioxide sediments at the bottle wall and/or the metal plate could be—partly significantly—reduced in all Examples of the present invention as compared to the Comparative Examples.

TABLE 3

| Example # | Thickening Agent | Active Substance | + Contaminant | Thickener (wt. %) | Wall Rating | Plate Rating |
|---|---|---|---|---|---|---|
| CE 84 | — | — | No | — | ++ | +++ |
| Example 44 | Dowfax 2A1 | branched C12-alkyl diphenyl oxide disulfonate | No | 0.3 | ++ | - |
| Example 45 | -"- | -"- | No | 0.6 | + | + |
| Example 46 | -"- | -"- | No | 0.9 | ++ | + |
| Example 47 | Laponite RD | synthetic sheet silicate | No | 5 | ++ | ++ |
| Example 48 | -"- | -"- | No | 10 | ++ | + |
| Example 49 | -"- | -"- | No | 15 | + | + |
| Example 50 | HDK D1515B | pyrogenic silicic acid | No | 5 | +++ | +++ |
| Example 51 | -"- | -"- | No | 10 | ++ | ++ |
| Example 52 | -"- | -"- | No | 15 | + | - |
| CE 85 | — | — | Yes | — | +++ | ++++ |
| Example 53 | Dowfax 2A1 | branched C12-alkyl diphenyl oxide disulfonate | Yes | 0.3 | +++ | +++ |
| Example 54 | -"- | -"- | Yes | 0.6 | ++ | ++ |
| Example 55 | -"- | -"- | Yes | 0.9 | + | ++ |
| Example 56 | LaponiteRD | synthetic sheet silicate | Yes | 5 | +++ | +++ |
| Example 57 | -"- | -"- | Yes | 10 | ++ | ++ |
| Examp e 58 | -"- | -"- | Yes | 15 | + | - |

Examples 59 Through 64 and Comparative Examples 86 and 87—Indicating Effect

In order to examine the amount at which permanganate provides for a well detectable color change in the compositions when reacted with organic contaminants, the following experiments were conducted.

Compositions each containing the following were prepared:

| | |
|---|---|
| $KMnO_4$ | 0.01 g |
| HC | 1.3 g |
| NaOH | 0.35 g |
| thickener | 0.9 g |
| water | to 1000 ml |

The thickener used in all cases of this series of experiments was Laponite RD. To these solutions, which therefore contained a permanganate concentration of 0.01 g/L, different amounts of additional $KMnO_4$ were added to give the concentrations listed in Table 4 below. These solutions were then sprayed onto a vertical ceramic tile wall to which a 0.01% glucose solution had been previously applied and dried in a manner analogous to Examples 30 through 42 to obtain a glucose amount of about 1 mg/100 cm² as the organic "contaminant" of the surface.

The color change of the indicator from purple to green due to the reduction of the permanganate was visually inspected on the surfaces sprayed with the compositions and evaluated as follows:
− Color change not at all or hardly visible
+ Color change visible with difficulties
++ Color change conveniently visible

TABLE 4

| | Color Change | | |
|---|---|---|---|
| Example # | $KMnO_4$ added (mg) | Conc. $KMnO_4$ (g/L) | Color change |
| CE 86 | 0 | 0.01 | - |
| Example 59 | 100 | 0.11 | + |
| Example 60 | 150 | 0.16 | ++ |
| Example 61 | 200 | 0.21 | ++ |
| Example 62 | 300 | 0.31 | ++ |
| Example 63 | 500 | 0.51 | ++ |
| Example 64 | 600 | 0.61 | + |
| CE 87 | 750 | 0.76 | - |

It can be seen that a color change generally suitable to detect non-contamination was visible starting from a permanganate concentration of 0.11 g/L and up to a concentration of 0.61 g/L. It was conveniently visible within a concentration range of from 0.16 to 0.51 g/L. With 0.01 g/L of permanganate the coloration of the composition was too pale, while that at 0.76 g/L was too intense to be clearly able to discern the color changes.

From this, one can derive a preferred concentration range for permanganate as an indicator of from about 0.1 to 0.6 g/L and an even more preferable range of from about 0.15 to 0.5 g/L.

In addition to the permanganate concentration ranges to be preferred, the examples above also clearly show that in such preferred embodiments of the present invention, permanganate is used not so much as an oxidant but rather as an indicating system, as the absence of color change shows that the oxidant contained next to permanganate has already eliminated all contaminants eligible for oxidation. Therefore, in these embodiments of the invention, the "additional oxidant" is in fact the main oxidant.

Example 65—Cleaning Effect

Considering the results of the Examples above, the ratio of the amounts of permanganate and additional oxidants as well as that amount of oxidants in the compositions which is at least required to effect thorough cleaning of surfaces from tenacious contaminants in addition to a detection effect within a relatively short exposure time were examined. To do that, the following mixtures were prepared, with the amount of hypochlorite being varied as indicated in Table 5 below:

| | |
|---|---|
| KMnO₄ | 0.01 g |
| HC | between 0.03 and 1.3 g |
| NaOH | 0.35 g |
| thickener | 0.9 g |
| water | to 1000 ml |

15 ml of a mixture of 40 g of malt extract and 8 g of diatomaceous earth (in 38 g of town water) were applied as an artificial contaminant difficult to remove on 15×15 cm steel plates with known weights and dried. Then, the above mixtures were sprayed on, each allowed to take effect for 2 minutes, then rinsed with 50 ml of water and dried The dried plates were then weighed to detect whether there were still organic residues on them.

In Table 5 below, the cleaning effect with respect to the artificial contaminant (48 g in total) was evaluated based on how much of it had remained on the respective plate:
-- >30 g
- <30 g, but >20 g
+ <20, but >10 g
++ <10 g

TABLE 5

| | Cleaning effect | |
|---|---|---|
| HC added (g) | Ratio HC:KMnO4 | Cleaning effect |
| 0.0 | — | -- |
| 0.03 | 3:1 | - |
| 0.05 | 5:1 | - |
| 0.10 | 10:1 | + |
| 0.20 | 20:1 | ++ |
| 0.30 | 30:1 | ++ |
| 0.50 | 50:1 | ++ |
| 1.30 | 130:1 | ++ |

This shows that the amount of "additional", or main, oxidant next to the permanganate indicator should be at least 10 times, more preferably at least 20 times the permanganate amount, and with regard to particularly fast cleaning, in particular at least 30 times the permanganate amount as well as that a concentration of at least 0.3 g/L of oxidant is required to be able to release surfaces from organic contaminants difficult to remove within a short period of time without leaving residues.

The above Examples thus show that not only did the use of a suitably selected thickening the compositions restrict flowability for a period of several minutes such that the compositions even adhered to vertical and downward facing surfaces, but also the stability of the oxidant could be increased and the formation of manganese dioxide effectively suppressed, thus improving the detectability of organic contaminants through simple color change and significantly reducing the formation of inorganic residues on the surfaces to be tested. Moreover, it was demonstrated that, when choosing suitable parameters, even organic surfactants can surprisingly be used as thickening agents in the compositions. When inorganic thickening agents are used, however, synthetic materials are preferable to natural ones as the latter—probably due to the presence of natural organic contaminants therein—may lead to false detection results.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of using a composition on an aqueous basis comprising a) at least one strong oxidant, b) a color indicating system, and c) one or more thickening agents, the method comprising:
   superficially applying the composition to a surface with organic substances; and
   detecting any contaminants on the surface by visual control after the superficial application,
   wherein the composition is not flowable for a predefined period after the superficial application due to an effect of the one or more thickening agents,
   wherein the one or more thickening agents are stable in the composition during the predefined period,
   wherein the one or more thickening agents are selected from the group consisting of synthetic sheet silicates, pyrogenic silicic acid, fatty alkyl (benzene) sulfates, sulfonates, carboxylates, phosphates and aminoxides and mixtures thereof, and
   wherein a color change in the composition superficially applied to the surface during the predefined period indicates organic contaminants being present on a portion of the surface, and
   wherein the one or more thickening agents have a stabilizing effect on the at least one strong oxidant, and wherein said one or more thickening agents produces a stabilizing effect on the color change when said composition reacts with any contaminants in the composition, such that the occurrence of false-positive detection results is reduced.

2. The method of claim 1, wherein the composition is applied to a vertical or downwards facing surface.

3. The method of claim 1, wherein the predefined period is at least 10 seconds.

4. The method of claim 1, wherein the at least one strong oxidant is selected from the group consisting of permanganates, peroxydisulfates, salts of halogen oxoacids and mixtures thereof.

5. The method of claim 1, wherein the at least one strong oxidant comprises permanganate.

6. The method of claim 5, wherein the at least one strong oxidant further comprises at least one additional oxidant whose oxidation potential exceeds that of permanganate.

7. The method of claim 6, wherein the at least one additional oxidant is selected from the group consisting of peroxydisulfate and hypochlorite.

8. The method of claim 5, wherein the permanganate at the same time serves as a color indicator.

9. The method of claim 8, wherein the permanganate is contained in the composition in an amount of 0.1 to 0.6 g/L or 0.01 to 0.06% by weight.

10. The method of claim 9, wherein the permanganate is contained in the composition in an amount of 0.15 to 0.4 g/L or 0.015 to 0.04% by weight.

11. The method of claim 6, wherein the at least one additional oxidant is contained in the composition in an amount that is at least 10 times, 20 times, or 30 times the amount of permanganate, or at a concentration of at least 0.3 g/L.

12. The method of claim 1, wherein the one or more organic thickening agents are contained in the composition in a total amount of not more than 3% by weight.

13. The method of claim 1, wherein the composition further contains one or more adjuvants selected from the group consisting of pH regulators, hardness stabilizers and biocides.

14. The method of claim 1, wherein the surface is at the same time cleaned by superficially applying the composition.

15. The method of claim 1, wherein the visual control is performed computer-assisted by conducting digital color comparisons.

* * * * *